United States Patent [19]
Johnson et al.

[11] Patent Number: 5,905,143
[45] Date of Patent: *May 18, 1999

[54] PURIFICATION OF PROTEINS

[75] Inventors: Richard A. Johnson, West Bridgford; Alan V. Quirk, Costock; John R. Woodrow, West Bridgford, all of United Kingdom

[73] Assignee: Delta Biotechnology Limited, Nottingham, United Kingdom

[ * ] Notice: This patent is subject to a terminal disclaimer.

[21] Appl. No.: 08/811,436

[22] Filed: Feb. 28, 1997

Related U.S. Application Data

[62] Continuation of application No. 08/398,484, Nov. 22, 1994, Pat. No. 5,625,041, which is a continuation of application No. 08/030,255, filed as application No. PCT/GB91/01556, Sep. 12, 1991, abandoned.

[30] Foreign Application Priority Data

Sep. 12, 1919 [GB] United Kingdom ................ 90 19919

[51] Int. Cl.$^6$ ...................................................... C07K 1/18
[52] U.S. Cl. ........................... 530/416; 530/364; 210/660; 210/668; 435/71.1; 435/71.2
[58] Field of Search .................................. 530/416, 364; 210/660, 668; 435/71.1, 71.2

[56] References Cited

U.S. PATENT DOCUMENTS

| | | | |
|---|---|---|---|
| 4,195,126 | 3/1980 | Hall | 435/11 |
| 4,374,930 | 2/1983 | Snoke et al. | 435/190 |
| 4,623,625 | 11/1986 | Scopes | 435/190 |
| 4,740,306 | 4/1988 | Litwack et al. | 530/417 |
| 4,990,447 | 2/1991 | König et al. | 435/71.1 |
| 5,136,026 | 8/1992 | Römisch et al. | 530/364 |
| 5,294,699 | 3/1994 | Ohmura | 530/416 |
| 5,625,041 | 4/1997 | Johnson et al. | 530/416 |

FOREIGN PATENT DOCUMENTS

| | | |
|---|---|---|
| 61/224996 | 10/1986 | Japan . |
| 63-83100 | 4/1988 | Japan . |
| 2/177893 | 7/1990 | Japan . |
| 1441625 | 2/1975 | United Kingdom . |
| 2053926 | 2/1981 | United Kingdom . |
| 9204367 | 3/1992 | WIPO . |

OTHER PUBLICATIONS

Jap. Soc. Biochem. "The Protein I–Separation, Purification and Properties", Tokyo Kakagu Dojin, 216 & 229 (Feb. 1990).

Harris, et al, ed., "Purification Methods", IRL Press (1989), pp. 245–246, 252–254, 258–261.

Travis et al, Biochem J. vol. 157, (1976) pp. 301–306.

Lascu et al, J. of Chromatography, vol. 283, (1984) pp. 199–210.

Bernabeu et al, Eur. J. of Biochem., vol. 189 (1980) pp. 285–290.

Wichman et al, Biochimica et Biophbica aeta, vol. 273 (1974) pp. 218–224.

Kyoritsu Shuppan "Extra Number: Protein, Nucleic Acid and Enzyme—Affinity Chromatography & Affinity Label", Kunihiko Ishikawa (ed.), (Mar. 1, 1980), pp. 66–71.

Scopes, Protein Purification, Principles and Practice (Springer Verlag. NY, 2nd Editio pp. 141–157), 1988.

Van Damme et al, J. Chromatog, vol. 57, pp. 158–160, 1971.

King, Transfusion, vol. 27, pp. 302–308, 1987.

Chem.Abs. 94127700v., 1981.

*Primary Examiner*—Chhaya D. Sayala
*Attorney, Agent, or Firm*—Naomi S. Biswas

[57] ABSTRACT

When proteins are purified using a protein-binding dye immobilized on a chromatographic matrix, the dye or a portion/derivative may leak into the eluant. An ion-exchange resin (e.g. Dowex-1) and a disrupting material (e.g. salt and a fatty acid such as sodium octanoate) are used to separate the dye from the protein to overcome the protein of the leaking dye.

5 Claims, 1 Drawing Sheet

PURIFICATION OF PROTEINS

CROSS-REFERENCE TO RELATED APPLICATION

This application is a continuation of U.S. patent application Ser. No. 08/398,484, filed on Nov. 22, 1994, now U.S. Pat. No. 5,625,041, which is a continuation of application Ser. No. 08/030,255, now abandoned, which is filed under 35 USC 371 as a national phase application of PCT/GB 91/01556 on Sep. 12, 1991.

The present invention relates to the purification of proteins. In this specification, the term "protein" includes naturally-occurring proteins, non-naturally-occurring proteins and other polypeptides which are large enough to have a ligand binding site, and the term "purification" means "rendering more pure", rather than conferring a given level of purity.

In the separation of proteins from natural sources or, particularly, from the media of fermentations in which a genetically engineered host cell produces the protein, a protein-containing liquid is often passed through a chromatographic column consisting of a protein-binding compound bound to a solid support. The protein-binding compound binds to a ligand-binding site on the protein whilst the other material passes through the column and the protein is later eluted from the column in a purer form.

However, a small proportion of the protein-binding compound and/or a portion thereof sometimes elutes with the protein and must later be separated from the protein, particularly if the protein is intended for medical use. There have been prior proposals simply to absorb the dye onto a column of cross-linked Sephadex (R.T.M., Pharmacia).

Scopes, R. K., in "Protein Purification, Principles and Practice" (Springer Verlag, N.Y., USA, 2nd Edition, pp 141–157), mentioned that trace amounts of dye in the eluate from dye-containing columns can be removed on anion exchangers but did not disclose whether it was the protein or the dye which should bind to the anion exchanger and did not mention the use of a disrupting agent. GB-A-2 053 296 disclosed the use of, amongst other things, a buffer containing sodium chloride and sodium caprylate to elute human serum albumin from an affinity medium. However, what those in the art would then have done, whether or not a dye contamination problem was perceived, was to dialyse away the salt and caprylate before further treatment. What we have now found is that combining the anion exchanger process with the use of a high salt/caprylate concentration to disrupt the dye-protein binding allows efficient separation of the dye from the desired protein.

Figure 1:
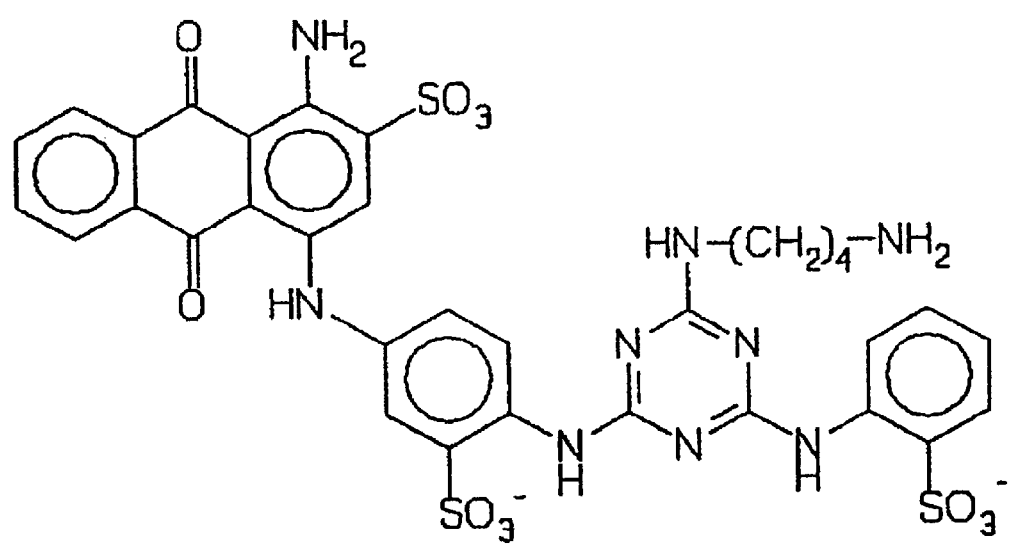
FIGURE 1 illustrates the structural formula of a dye useable to purify human albumin.

Accordingly, one aspect of the present invention provides a process for removing some or all of a protein-binding compound from an aqueous liquid containing the protein-binding compound and a protein to which it can bind or is bound, the process comprising the steps of (1) exposing the liquid to a disrupting material to disrupt binding of the protein to the protein-binding material, (2) exposing the liquid to an ion exchange resin to bind the protein-binding material to the resin and (3) separating the resin from the liquid.

Steps (1) and (2) may be simultaneous or may at least overlap such that the liquid is still exposed to the disrupting agent at the time that it is exposed to the resin. Step (3) is usually performed by passing the liquid through a column of the resin such that a solution of the protein, relatively free of the protein-binding material, is obtained.

The process is particularly well suited to removing synthetic textile dye compounds of the sort which have been disclosed in the literature for purifying proteins. Many such proteins (probably thousands) can be purified by the use of such dyes. To pick just one dye, Cibacron Blue 3-GA, this can be used to purify kinases, dehydrogenases and most other enzymes requiring adenyl-containing co-factors, for example $NADP^+$ and $NAD^+$. Such proteins include alcohol dehydrogenase, adenylate cyclase, adenylate kinase, glucose-6-phosphate dehydrogenase, hexokinase, phosphofructokinase and glyceraldehyde-3-phosphate dehydrogenase. Although the Cibacron Blue 3-GA dye will bind to these classes of proteins, it is also possible to use the Cibacron Blue 3-GA dye to purify proteins that do not have the dinucleotide binding site. These include albumin, lipoproteins, blood coagulation factors, interferon and thyroxin binding globulin. These dye compounds are usually anionic, in which case an anion-exchanger is most appropriate in the process of the invention, but some are cationic, in which case a cation-exchanger is most appropriate. The protein-binding compound is preferably a polysulphonated aromatic compound and is most preferably a triazine dye. Procion Brown MX-5BR, Cibacron Blue 3-GA, (suitable for separating human serum albumin), Procion Red H-8BN (for carboxypeptidase G2), Procion Yellow MX-AG (for IMP dehydrogenase), Procion Red HE-3B (for lactate dehydrogenase), Procion Green H-4G (for hexokinase), Procion Blue MX-4GD (for malate dehydrogenase), Procion Red H-3B (for 3-hydroxybutyrate dehydrogenase) and Procion Blue MX-R (for L-lactate dehydrogenase) are examples. These and others are summarised in the following table:

| Group 1 | Group 2 | Group 3 | Group 4 | Group 5 |
|---|---|---|---|---|
| P Blue MX-7RX | R Black GF | P Blue H-EG | P Black H-EXL | P Blue H-ERD |
| C Blue 2-RA | P Blue MX-R | P Blue H-EGN | P Blue H-GR | C Blue F-R |
| R Orange 3R | P Brown MX-GRN | P Blue H-4R | P Blue MX-G | P Brown H-5R |
| P Red MX-2B | C Brown 3-GRA | P Blue MX-3G | P Blue MX-4GD | P Green H-4G |
| P Rubine H-BN | P Navy H-4R | C Blue F3-GA | D Blue K-BL | P Green H-E4BD |
| P Turquoise H-A | P Orange MX-G | R Blue B | P Brown H-3R | P Navy H-ER |
| P Turquoise MX-G | R Orange FR | R Blue R | P Brown MX-5BR | P Red H-3B |
| C Turquoise 6-GE | P Red MX-5B | C Navy F-2R | P Orange H-ER | P Red H-8BN |
| R Violet R | P Scarlet MX-G | P Red H-E3B | P Orange MX-2R | P Red H-E7B |
| R Yellow GNL | P Scarlet MX-3G | P Rubine MX-B | P Red MX-7B | P Scarlet H-E3G |
| P Yellow H-A | C Turquoise GFP | P Scarlet H-2G | P Red MX-8B | P Yellow H-E3G |
| P Yellow MX-6G | C Yellow R-A | P Yellow H-E6R | C Red 3-BA | P Yellow H-E6G |

-continued

| Group 1 | Group 2 | Group 3 | Group 4 | Group 5 |
| --- | --- | --- | --- | --- |
| P Yellow MX-8G | P Yellow MX-3G | P Yellow H-5G | P Violet H-3R | P Yellow H-E4R |
|  | P Yellow MX-4R | P Yellow MX-R | P Yellow H-E6R | P Yellow MX-GR |
|  |  | C Yellow 3-GP |  |  |

Group 1 dyes bind the least protein from crude extracts of tissues, and group 5 dyes the most. Actual groups may vary ± 1 with different types of extract. P, I.C.I. Procion; C, Ciba-Geigy Cibacron; R, Hoechst Remazol; D, Sandoz Drimarene. Not all of these dyes are still commercially available. Source: From J. Chromatogr. 376, 131–140 (1986)

The dye itself (with or without the spacer which is commonly used to attach the dye to a column) may cause the contamination, or the problem may be caused by a derivative of the dye or an intermediate used in the synthesis of the dye.

Cation-exchangers include S and CM Fast Flow, from Pharmacia.

Anion-exchangers include Pharmacia's DEAE Fast Flow and Q Fast Flow. Preferably, the matrix is Dowex-1, which is a strongly basic anion exchange resin, preferably 2% cross-linked, with a dry mesh size of 50–100. Generally, a strong anion exchanger is better than a weak exchanger.

The protein may be a serum-derived protein such as human albumin, a lipoprotein, a blood coagulation factor such as Factor VIII or Factor IX, thyroxin-binding globulin or alpha interferon. Preferably, the protein is human albumin (HA) or a mutant or fragment thereof which retains a dye-binding domain (such as is described in EP-A-322 094 published Jun. 28, 1989) or a fusion of HA or a said mutant or fragment with another protein. The aqueous liquid is suitably the direct or indirect result of exposing a fermentation medium or fractions thereof to the protein-binding compound; "indirect" in this context means that the fermentation medium, after contact with the protein-binding compound, may be treated in one or more process steps before the process of the invention is applied. By "fermentation medium" we mean the medium which results from the fermentation of an organism capable of producing the protein. The organism (which term includes cell lines) is preferably transformed or transfected to produce the protein and the protein is normally heterologous to the. organism. The organism may be a bacterium (eg E. coli or B. subtilis), a yeast (eg Saccharomyces cerevisiae), a non-yeast fungus (eg Aspergillus tiger) , an insect cell (eg Spodoptera frugiperda), a plant cell (eg a hairy root cell culture of Atropa belladonna) or a mammalian cell (eg Vero cells). Preferably, the organism is a yeast. Exemplary genera of yeast contemplated to be useful in the practice of the present invention are Pichia, Saccharomyces, Kluyveromyces., Candida, Torulopsis, Hansenula, Schizosaccharomyces, Citeromyces, Pachysolen, Debaromyces, Metschunikowia, Rhodosporidium, Leucosporidium, Botryoascus, Sporidiobolus, Endomycopsis, and the like. Preferred genera are those selected from the group consisting of Pichia, Saccharomyces, Schizosaccharomyces, Kluyveromyces, Yarrowia and Hansenula, because the ability to manipulate the DNA of these yeasts has, at present, been more highly developed than for the other genera mentioned above.

Examples of Saccharomyces are Saccharomyces cerevisiae (especially preferred), Saccharomyces italicus and Saccharomyces rouxii. Examples of kluyveromyces are Kluyveromyces fraqilis and Kluyveromyces lactis. Examples of Hansenula are Hansenula polymorpha, Hansenula anomala and Hansenula capsulata. Yarrowia lipolytica is an example of a suitable Yarrowia species, and Schizosaccharomyces pombe is a further suitable yeast.

The production of human albumin expressed from a gene inserted into a suitable host by recombinant DNA techniques is well known in the art and does not require discussion herein. Examples of specific prior art processes include those described in EP-A-147 198 (Delta Biotechnology), EP-A-201 239 (Delta), EP-A-60 057 (Genentech), EP-A-88 632 (Genentech), EP-A-251 744 (Delta) and EP-A-286 424 (Delta).

Similarly, processes for purifying proteins from a fermentation medium are known in the art. A good review may be found in "Protein Purification—Principles and Practice", 2nd Edition (Springer Verlag, N.Y.), especially pages 141–157.

Preferably, the aqueous liquid results from passing the fermentation medium through one or more separation (eg chromatographic) steps.

It is to be noted that, although the process of the invention is particularly well suited to separating a protein-binding compound from a protein when the protein-binding compound has been used to purify the protein from, for example, a fermentation medium or a product thereof, the process can generally be used to separate any suitable protein-binding contaminant from a protein. An advantage of the process is that it does not require binding o. the protein to the resin and hence relatively large volumes of protein can be purified for a given volume of resin.

The disrupting material may be a single compound or a mixture. Preferably, it comprises a mixture of a salt (preferably sodium chloride or potassium chloride) and a compound to disrupt hydrophobic interactions between the protein and the protein-binding compound, for example a (preferably non-ionic) detergent, an organic so sent or, preferably, a fatty acid. Alternative disrupters of hydrophobic interactions with the protein include N-acetyltryptophan and mandelic acid, which will normally be used as their salts, for example sodium salts. The fatty acid is preferably octanoic acid but other fatty acids (preferably $C_6$–$C_{10}$ and preferably saturated) may be used. The fatty acid will usually be present in the form of its salt, for example the sodium salt. The concentrates of the salt and fatty acid may be varied to suit the particular protein and protein-binding compound in question. A salt concentration of 0.1 M to 3 M will generally be useful, preferably 0.5 to 2.0 M. A fatty acid concentration of 10 mM–100 mM is generally useful, preferably 25–60 MM, most preferably about 50 mM. When the disrupting material is a single compound, any of these materials may be used.

The liquid which is exposed to the ion exchange resin will usually consist largely of the buffer used to elute the protein from the column containing the protein-binding compound. The disrupting material or a component of it may then be added. For example, if the elution buffer contains 2 M NaCl in a 50 mM phosphate buffer of pH 7.0, there may be no need to add further salt, and only the fatty acid is added. The pH can be altered if desired. We have found that a pH of about 7.0 is suitable, but generally any pH of above 5.0 is applicable to any fatty acid.

The pH should preferably be such that the protein-binding compound is charged; for example most polysulphonated triazine dyes are negatively charged above pH 2 to 3. It is not always necessary for the liquid to contain a buffer.

The most convenient means of exposing the mixture of the protein and protein-binding compound to the ion exchange resin and disrupting material will be to add the disrupting material to the mixture and then to pass the resulting liquid through a column of the ion exchange resin. This minimises the amounts of buffer and resin used, and the amount of protein lost. However, it is technically possible to expose the protein/protein binding compound mixture to the resin first, and then to elute the protein with a buffer containing the disrupting material. A larger column of resin will usually be needed in such an embodiment, which will then probably have to be cleaned stringently with suitable acids and solvents rather than being simply discarded.

The columns may be the conventional linear type or radial flow cartridges.

The invention will now be illustrated by way of example and with reference to FIGURE 1 which shows the structure of a textile dye (Cibacron Blue 3-GA) and spacer (4-amino butyl group usable in a column to purify human albumin.

EXAMPLE 1

As a model of the product of passing an HA-containing fermentation medium through a purification column, a 3 mg.ml$^{-1}$ solution of human serum albumin was prepared in 2 M NaCl, 50 mM phosphate buffer pH 7.0, and 21 $\mu$g.ml$^{-1}$ of Cibacron Blue dye covalently attached to a spacer (FIGURE 1) was added. The dye included a spacer used to attach the dye molecule to the matrix and also a dye synthesis intermediate. 1 M sodium octanoate, as the disrupter of hydrophobic interactions, was added to give a concentration of 50 mM. This solution (20 ml) was then passed through a 1 ml column of Dowex-1 resin (2% cross-linked; Dow Chemical Co) at a flow rate of 0.5 ml.min$^{-1}$. The removal of blue dye from HA was measured spectrophotometrically at 620 nm.

Under these conditions, about 97% of the blue dye bound to the resin. The unbound fraction which had passed through the column contained greater than 97% of the HA applied to the column.

EXAMPLE 2

Following the procedure of Example 1, the efficiency of dye removal from HA was assessed in the presence of buffer, 2 M NaCl, caprylate and combinations of these components. As can be seen from the results in Table 1, a combination of salt and fatty acid was much more effective than the individual components.

TABLE 1

| Buffer | | Dye + Spacer Removal (%) | Dye Intermediate Removal (%) |
|---|---|---|---|
| A | 50 mM phosphate pH 7.0 | 19 | N/D |
| B | 50 mM phosphate + 2 M NaCl | 32 | N/D |
| C | 50 mM phosphate + 50 MM caprylate | 46 | N/D |
| D | Combination (B + C) | 97 | 96 |

N/D = not determined

EXAMPLE 3

The comparison of Example 2 was repeated, using Cibacron Blue 3-GA (Blue), Procion Green H-4G (Green), Procion Brown MX-5BR (Brown) and Procion Red HE-3B (Red) dyes covalently attached to a spacer. The results are shown in Table 2.

TABLE 2

| | HSA/Dye + Spacer Separation (% removal) | | | |
|---|---|---|---|---|
| Buffer | Blue | Green | Brown | Red |
| A | 19 | 11 | 52 | 33 |
| B | 32 | 41 | 93 | 57 |
| C | 46 | 45 | 90 | 83 |
| D | 97 | 65 | 89 | 92 |

A–D as Table 1

EXAMPLE 4

The experiment of Example 2 was repeated with different proteins. The results are shown in Table 3. Alkaline phosphatase was mixed with blue or red dyes.

TABLE 3

| | Protein/Dye + Soacer Separation (% removal) | | | | | |
|---|---|---|---|---|---|---|
| Buffer | HSA | LACTOFERRIN | ADH | GK | AP/Blue | AP/Red |
| A | 19 | 66 | N/D | N/D | 52 | N/D |
| B | 32 | N/D | 42 | 73 | 80 | 63 |
| C | 46 | 67 | 72 | 96 | 80 | 71 |
| D | 97 | 81 | 94 | 91 | 84 | 92 |

A–D as Table 1
GK = glycerokinase
ADH = alcohol dehydrogenase
AP = alkaline phosphatase
N/D = not determined

We claim:

1. In a process for purifying a protein, said process comprising:

(a) providing a chromatographic column comprising a solid support and bound thereto a protein-binding compound which will releasably bind the protein;

(b) passing a solution of the protein through the column such that the protein-binding compound releasably binds the protein; and (c) eluting the protein from the column to yield a liquid containing protein and any protein-binding compound in bound form that eludes; wherein the improvement comprises the further steps of:

(d) exposing the liquid to an ion exchange resin under conditions such that the ion exchange resin does not directly bind the protein, but does bind the protein-binding compound; and (e) separating the resin having the protein-binding compound bound thereto from the liquid containing said protein, wherein, prior to either step (d) or step (e), the liquid is exposed to a disrupting material to disrupt binding of said protein to said protein-binding compound, said disrupting material comprising a mixture of a salt and a compound, other than said protein-binding compound, which disrupts hydrophobic interactions between the protein and said protein-binding compound.

2. A process according to claim 1, wherein said steps (d) and (e) are carried out simultaneously by passing said aqueous liquid through a column containing said resin and eluting said column with a suitable liquid.

3. A process in accordance with claim 1, wherein said disrupting material is admixed with said aqueous liquid prior to passage through said column.

4. A process in accordance with claim 1, where said disrupting material is admixed with said liquid utilized to elute said column.

5. A process in accordance with claim 1, wherein the compound which disrupts hydrophobic interactions between the protein and said protein-binding compound is a fatty acid or a salt thereof.

* * * * *